(12) United States Patent
Glauser et al.

(10) Patent No.: US 8,703,167 B2
(45) Date of Patent: Apr. 22, 2014

(54) COATINGS FOR IMPLANTABLE MEDICAL DEVICES FOR CONTROLLED RELEASE OF A HYDROPHILIC DRUG AND A HYDROPHOBIC DRUG

(75) Inventors: Thierry Glauser, Redwood City, CA (US); Irina Astafieva, Palo Alto, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1320 days.

(21) Appl. No.: 11/447,551

(22) Filed: Jun. 5, 2006

(65) Prior Publication Data

US 2007/0280991 A1 Dec. 6, 2007

(51) Int. Cl.
*A61F 2/02* (2006.01)
*A61K 31/4745* (2006.01)
*C08G 63/91* (2006.01)

(52) U.S. Cl.
USPC .......................... 424/423; 424/426; 525/54.1

(58) Field of Classification Search
None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 3,886,125 A | 5/1975 | Chromecek |
| 3,893,988 A * | 7/1975 | Seymour et al. ............... 526/320 |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,213,580 A | 5/1993 | Slepian et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,383,928 A | 1/1995 | Scott et al. |
| 5,417,981 A | 5/1995 | Endo et al. |
| 5,419,760 A * | 5/1995 | Narciso, Jr. ....................... 604/8 |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,575,815 A | 11/1996 | Slepian et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,607,475 A | 3/1997 | Cahalan et al. |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

International Search Report for PCT/US2007/013327, filed May 6, 2007, mailed Nov. 30, 2007, 14 pgs.

(Continued)

*Primary Examiner* — Robert A Wax
*Assistant Examiner* — Danah Al-Awadi
(74) *Attorney, Agent, or Firm* — Squire Sanders (US) LLP

(57) ABSTRACT

Provided herein is a coating that includes cRGD for endothelial cells and methods of making and using the same.

28 Claims, No Drawings

(56) References Cited

U.S. PATENT DOCUMENTS

| | | | |
|---|---|---|---|
| 5,702,754 A | 12/1997 | Zhong | |
| 5,711,958 A | 1/1998 | Cohn et al. | |
| 5,716,981 A | 2/1998 | Hunter et al. | |
| 5,721,131 A | 2/1998 | Rudolph et al. | |
| 5,723,219 A | 3/1998 | Kolluri et al. | |
| 5,725,568 A | 3/1998 | Hastings | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,782,908 A | 7/1998 | Cahalan et al. | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,834,408 A | 11/1998 | Mishra et al. | |
| 5,837,008 A | 11/1998 | Berg et al. | |
| 5,837,313 A | 11/1998 | Ding et al. | |
| 5,843,156 A | 12/1998 | Slepian et al. | |
| 5,849,859 A | 12/1998 | Acemoglu | |
| 5,851,508 A | 12/1998 | Greff et al. | |
| 5,854,376 A | 12/1998 | Higashi | |
| 5,857,998 A | 1/1999 | Barry | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,874,165 A | 2/1999 | Drumheller | |
| 5,876,433 A | 3/1999 | Lunn | |
| 5,877,224 A | 3/1999 | Brocchini et al. | |
| 5,879,713 A | 3/1999 | Roth et al. | |
| 5,880,220 A | 3/1999 | Warzelhan et al. | |
| 5,891,192 A | 4/1999 | Murayama et al. | |
| 5,897,955 A | 4/1999 | Drumheller | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,182 A | 6/1999 | Drumheller | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,096 A | 9/1999 | Santos et al. | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,087,479 A | 7/2000 | Stamler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,174,539 B1 | 1/2001 | Stamler et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,290,729 B1 * | 9/2001 | Slepian et al. | 623/23.72 |
| 6,299,604 B1 | 10/2001 | Ragheb et al. | |
| 6,306,166 B1 | 10/2001 | Barry et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,379 B1 | 4/2002 | Wang | |
| 6,379,381 B1 | 4/2002 | Hossainy et al. | |
| 6,379,382 B1 | 4/2002 | Yang | |
| 6,383,500 B1 | 5/2002 | Wooley et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,471,978 B1 | 10/2002 | Stamler et al. | |
| 6,475,779 B2 | 11/2002 | Mathiowitz et al. | |
| 6,482,834 B2 | 11/2002 | Spada et al. | |
| 6,494,862 B1 | 12/2002 | Ray et al. | |
| 6,497,729 B1 | 12/2002 | Moussy et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,408 B1 | 1/2003 | Palasis | |
| 6,506,437 B1 | 1/2003 | Harish et al. | |
| 6,514,734 B1 | 2/2003 | Clapper et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,548,637 B1 * | 4/2003 | Persons et al. | 530/331 |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,613,082 B2 | 9/2003 | Yang | |

(56) References Cited

U.S. PATENT DOCUMENTS

| | | |
|---|---|---|
| 6,613,084 B2 | 9/2003 | Yang |
| 6,613,432 B2 | 9/2003 | Zamora et al. |
| 6,616,765 B1 | 9/2003 | Castro et al. |
| 6,620,617 B2 | 9/2003 | Mathiowitz et al. |
| 6,623,448 B2 | 9/2003 | Slater |
| 6,623,521 B2 | 9/2003 | Steinke et al. |
| 6,625,486 B2 | 9/2003 | Lundkvist et al. |
| 6,641,611 B2 | 11/2003 | Jayaraman |
| 6,645,135 B1 | 11/2003 | Bhat |
| 6,645,195 B1 | 11/2003 | Bhat et al. |
| 6,652,575 B2 | 11/2003 | Wang |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,703,466 B1 | 3/2004 | Karakelle et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 7,008,667 B2 | 3/2006 | Chudzik et al. |
| 7,063,884 B2 | 6/2006 | Hossainy et al. |
| 7,094,256 B1 | 8/2006 | Shah et al. |
| 7,247,313 B2 | 7/2007 | Roorda et al. |
| 8,110,211 B2 | 2/2012 | Pacetti et al. |
| 8,309,112 B2 | 11/2012 | Glauser et al. |
| 8,323,676 B2 | 12/2012 | Lim et al. |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0013437 A1 | 1/2002 | McKee et al. |
| 2002/0026236 A1 | 2/2002 | Helmus et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0082680 A1* | 6/2002 | Shanley et al. .............. 623/1.16 |
| 2002/0087123 A1 | 7/2002 | Hossainy et al. |
| 2002/0091433 A1 | 7/2002 | Ding et al. |
| 2002/0094440 A1* | 7/2002 | Llanos et al. ................. 428/421 |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0108588 A1* | 6/2003 | Chen et al. .................... 424/423 |
| 2003/0113439 A1 | 6/2003 | Pacetti et al. |
| 2003/0129130 A1* | 7/2003 | Guire et al. .................. 424/1.11 |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0199964 A1 | 10/2003 | Shalaby et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0033251 A1* | 2/2004 | Sparer et al. .................. 424/425 |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0106985 A1 | 6/2004 | Jang |
| 2004/0172121 A1 | 9/2004 | Eidenschink et al. |
| 2004/0172127 A1 | 9/2004 | Kantor |
| 2004/0228831 A1* | 11/2004 | Belinka et al. ............. 424/78.27 |
| 2004/0236415 A1 | 11/2004 | Thomas |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0095267 A1 | 5/2005 | Campbell et al. |
| 2005/0106203 A1* | 5/2005 | Roorda et al. .................. 424/423 |
| 2005/0106210 A1 | 5/2005 | Ding et al. |

(56) References Cited

U.S. PATENT DOCUMENTS

| | | | |
|---|---|---|---|
| 2005/0113903 A1 | 5/2005 | Rosenthal et al. | |
| 2005/0137715 A1 | 6/2005 | Phan et al. | |
| 2005/0147647 A1 | 7/2005 | Glauser et al. | |
| 2005/0181015 A1* | 8/2005 | Zhong | 424/426 |
| 2005/0232970 A1* | 10/2005 | Stucke et al. | 424/426 |
| 2005/0233062 A1 | 10/2005 | Hossainy et al. | |
| 2005/0244453 A1* | 11/2005 | Stucke et al. | 424/423 |
| 2005/0245637 A1 | 11/2005 | Hossainy et al. | |
| 2005/0288481 A1 | 12/2005 | DesNoyer et al. | |
| 2006/0067908 A1* | 3/2006 | Ding | 424/78.27 |
| 2006/0078493 A1 | 4/2006 | Von Oepen | |
| 2006/0105099 A1* | 5/2006 | Takahashi et al. | 427/2.1 |
| 2006/0280771 A1 | 12/2006 | Groenewegen et al. | |
| 2007/0280991 A1 | 12/2007 | Glauser et al. | |
| 2009/0258028 A1 | 10/2009 | Glauser et al. | |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 89/06957 | 8/1989 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/003890 | 1/2002 |
| WO | WO 02/026162 | 4/2002 |
| WO | WO 02/034311 | 5/2002 |
| WO | WO 02/055122 | 7/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/000383 | 12/2003 |
| WO | WO 2004/009145 | 1/2004 |
| WO | WO 2005/053937 | 6/2005 |
| WO | WO 2005/081878 | 9/2005 |
| WO | WO 2005/092406 | 10/2005 |
| WO | WO 2006/031532 | 3/2006 |
| WO | WO 2006/112932 | 10/2006 |

OTHER PUBLICATIONS

U.S. Appl. No. 10/871,658, filed Jun. 18, 2004, Hossainy et al.
Anonymous, *Cardiologists Draw-Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Adessi et al., *Solid phase DNA amplification: characterization of primer attachment and amplification mechanisms*, Nucleic Acids Research, vol. 28, No. 20 (2000).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable. Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Gombotz et al., *Biodegradable Polymers for Protein and Peptide Drug Delivery*, Bioconjugate Chem. 6, 332-351 (1995).
Grabarek et al. *Zero-Length Crosslinking Procedure with the Use of Active Esters*, Anal. Biochemistry 185, 131-135 (1990).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).

(56) References Cited

OTHER PUBLICATIONS

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Kipshidze et al., *Role of the Endothelium in Modulating Neointimal Formation*, J. of Am. College of Cardiology, vol. 44, No. 4, 733-739 (2004).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polyethers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Serruys et al., *A Randomized Comparison of the Value of Additional Stenting After Optimal Balloon Angioplasty for Long Coronary Lesions*, J. of Am. College of Cardiology, vol. 39, No. 3, 393-399 (2002).

Shigeno, *Prevention of Cerebrovascular Spasm by Bosentan*, Novel Endothelin Receptor, Chemical Abstract 125:212307 (1996).

va Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriathycin in polymeric micelles and their design for in vivo delivery to a solid tumor*, Journal of Controlled Release 50:79-92 (1998).

Blindt et al. "A Novel Drug-Eluting Stent Coated with an Integrin-Binding Cyclic Arg-Gly-Asp peptide Inhibits Neointimal Hyperplasia by Recruiting Endothelial Progenitor Cells", J. of the Am. College of Cardiology vol. 47, No. 9, pp. 1786-1795 (2006).

Gombotz et al., "Biodegradable Polymers for Protein and Peptide Drug Delivery", Bioconjugate Chem. 6, pp. 332-351 (1995).

Lutolf et al., "Synthesis and Physicochemical Characterization of End-Linked Poly (ethylene glycol) co-peptide Hydrogels Formed by Michael-Type Addition", Biomacromolecules 4(3) pp. 713-722 (2003).

Rudin, "The Elements of Polymer Science and Engineering", 2$^{nd}$ Ed. book, 8 pgs.

Yoshikawa et al. "Monolayer properties of mixtures of poly (n-Butyl methacrylate) and poly (n-Lauryl methacrylate), and their corresponding copolymers", Colloid & Polymer Sci. 256, pp. 422-426 (1978).

\* cited by examiner

COATINGS FOR IMPLANTABLE MEDICAL DEVICES FOR CONTROLLED RELEASE OF A HYDROPHILIC DRUG AND A HYDROPHOBIC DRUG

BACKGROUND

1. Field of the Invention

This invention is generally related to coatings containing cRGD for implantable medical devices, such as drug delivery vascular stents.

2. Description of the State of the Art

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, ISR still poses a significant problem given the large-volume of coronary interventions and their expanding use. The pathophysiological mechanism of ISR involves interactions between the cellular and acellular elements of the vessel wall and the blood. Damage to the endothelium during PCI constitutes a major factor for the development of ISR (see, e.g., Kipshidze, N., et al., J. Am. Coll. Cardiol. 44:733-739 (2004)).

Further, in the art of drug delivery stent, it is often desirable that the stent is capable of concurrent release of a hydrophilic drug and a hydrophobic drug. However, the controlled release of a hydrophilic drug and a hydrophobic drug can be challenging due to the heterogeneous natures of the two types of drugs.

Therefore, there is a need for a coating for controlled and sustained release of an attractant for endothelial progenitor cells. There is a further need for a coating capable of controlled release of an agent capable of reducing the incidence of in-stent restenosis after PCI. There is a further need for a coating capable of controlled release of a hydrophilic drug and a hydrophobic drug.

The embodiments of the present invention address these concerns as well as others that are apparent to one having ordinary skill in the art.

SUMMARY

Provided herein is a coating capable of controlled release of a hydrophilic drug (e.g., cRGD peptide) and a hydrophobic drug such as an anti-proliferative agent. In some embodiments, the hydrophilic drug is a cRGD peptide which can be attached to a coating while the hydrophobic drug is an anti-proliferative agent such as everolimus.

In some embodiments, the present invention provides a coating having a construct capable of controlled release of a hydrophilic drug and a hydrophobic drug. In some embodiments, the hydrophilic drug can be included in a layer that includes a polymer having polar block(s) or segment(s). The hydrophobic drug can be included in a layer that includes a hydrophobic polymer and the hydrophobic drug. In some embodiments, the layer containing the hydrophilic drug and the layer containing the hydrophobic drug can be separated with a sealant layer. The sealant layer can include a hydrophobic polymer such as hydrophobic acrylates or fluoropolymers. Preferably, the hydrophilic drug is a cRGD peptide and the hydrophobic drug is an anti-proliferative agent such as everolimus.

In some embodiments, the coating can further include a bioactive agent that is not the hydrophilic drug or the hydrophobic drug described above.

The coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

Provided herein is a coating capable of controlled release of a hydrophilic drug (e.g., cRGD peptide) and a hydrophobic drug such as an anti-proliferative agent. In some embodiments, the hydrophilic drug is a cRGD peptide which can be attached to a coating while the hydrophobic drug is an anti-proliferative agent such as everolimus. cRGD is a hydrophilic chemo-attractant for endothelial progenitor cells (EPCs). The anti-proliferative such as everolimus can reduce the incidence of resteonosis.

In some embodiments, the present invention provides a coating having a construct capable of controlled release of a hydrophilic drug and a hydrophobic drug. In some embodiments, the hydrophilic drug can be included in a layer that includes a polymer having polar block(s) or segment(s). The hydrophobic drug can be included in a layer that includes a hydrophobic polymer and the hydrophobic drug. In some embodiments, the layer containing the hydrophilic drug and the layer containing the hydrophobic drug can be separated with a sealant layer. The sealant layer can include a hydrophobic polymer such as hydrophobic acrylates or fluoropolymers. Preferably, the hydrophilic drug is a cRGD peptide and the hydrophobic drug is an anti-proliferative agent such as everolimus.

In some embodiments, the coating can further include a bioactive agent that is not the hydrophilic drug or the hydrophobic drug described above.

The term "cRGD peptide" includes any proteins or peptides that comprise cRGD. cRGD stands for cyclic RGD. The RGD (tri-peptide) sequence can be found in numerous proteins and extra-cellular matrix, as well as in short peptides whether they are linear, cyclic, free or linked. The nature of the adjacent peptides and the structure of the molecule may be critical for efficacy. Therefore, the term "cRGD" can be used interchangeably with the term "RGD peptide." In some embodiments, the cRGD peptide includes cRGD peptide mimetics.

The term "anti-proliferative" as used herein, refers to an agent that works to block the proliferative phase of acute cellular rejection. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. The anti-proliferatives described herein are generally hydrophobic.

The coating described herein can be formed on a medical device for treating, preventing, or ameliorating a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

Attaching a Hydrophilic Drug to a Coating

In some embodiments, a hydrophilic drug (e.g., a cRGD peptide) can be attached to the coating via a spacer, which can be degradable or durable. In some embodiments, the spacer is a degradable spacer. A degradable spacer is one that can be hydrolytically or enzymetically degraded in vivo. Such a degradable spacer can have, e.g., an ester linking group or another group such as a thiol or an amide. Where the spacer or linker of a cRGD to a coating is degradable (e.g., by degradation by hydrolysis or proteolysis or by enzymatic degradation), the degradation of this linkage or spacer can dictate the release rate of the hydrophilic drug (e.g., a cRGD peptide). An example of the degradable linkage is an ester bond. An example of the hyodrphilic drug is a cRGD peptide. An example of the hydrophobic drug is an anti-proliferative agent such as everolimus.

In some embodiments, a coating can contain functional groups that allow the attachment of a hydrophilic drug to the coating. For example, the functional group can include groups capable of forming ester bonds with a linker or spacer attached to the hydrophilic drug. In these embodiments, the topcoat shall have sufficient density of the functional groups to allow sufficient amount of the hydrophilic drug (e.g., a cRGD peptide) to attach to the coating. Where the hydrophilic drug is a cRGD peptide, the drug load requirement in the coating is the amount sufficient for recruiting endothelial progenitor cells.

The attachment of a hydrophilic drug such as a cRGD peptide to the coating can be achieved via two mechanisms. In some embodiments, the hydrophilic drug can be attached to, a polymer via a spacer or linker. The polymer with the hydrophilic drug attached thereto can then be sprayed onto a medical device. In some embodiment, the hydrophilic drug can be attached to a polymer coating so as to generate a coating with hydrophilic drug attached thereto, which sometimes can be referred to as surface treatment of the coating.

The attachment of a hydrophilic drug (e.g., a cRGD peptide) to a polymer (a free polymer or a polymer in a coating) having functional groups via established procedures in the art of organic synthesis (see, for example, Larock, Comprehensive Organic Transformations: A Guide to Functional Group Preparations, John Wiley & Sons, Inc., Copyright 1999). For example, in some embodiments, the polymer can have hydroxyl groups, which can form an ester bond with a carboxylic group of hydrophilic drug or a carboxylic group on a linker or spacer molecule. In some embodiments, the polymer can have carboxylic groups, which can form ester bonds with hydroxyl groups on a linker or spacer molecule.

In some other embodiments, the attachment of a hydrophilic drug can be achieved via forming an imine Schiff base. For example, a polymer can be modified to have linkers or spacers having a CHO, which can form the imine Schiff base with the amine group on a hydrophilic drug. The imine Schiff base is hydrolytically unstable and can release the hydrophilic drug under in vivo conditions.

In some embodiments, the polymer can be modified to include a linker or spacer having a CHO or keto group, while the hydrophilic drug can be modified to include a spacer/linker having a hydroxyl group(s). The attachment of a hydrophilic drug to a polymer can be achieved via forming an acetal or hemi-acetal by reaction of the aldehyde or keto group with the hydroxyl group(s). The acetal or hemi-acetal can undergo hydrolysis under in vivo conditions to release the hydrophilic drug.

In some embodiments, a hydrophilic drug can be attached to a polymer (a free polymer or polymer in a coating) via DCC or EDC chemistry, which is well documented in the art of solid phase peptide chemistry (see, e.g., Grabarek, Z. and Gergely, J. Anal. Biochem. 185:131-135 (1990); Adessi, et al., Nucleic Acids Res. 28(20): e87 (2000)). The hydrophilic drug thus attached can be released upon hydrolytic degradation of the linkage.

Linkers

In some embodiments, the chemo-attractant can be attached to a polymer matrix via a labile linker or via physical interactions such as interpenetrating networks. The labile linker can be a linker sensitive to a stimulus. For example, the linker can be a hydrolytically degradable linker or an enzymetically degradable linker.

Hydrolytically degradable linkers can degrade under physiological conditions in the presence of water. In other words, the stimulus for a hydrolytically degradable linker is the presence of water. A hydrolytically degradable linker can link the chemo-attractant and the polymer via the linker's reactive groups. For example, in some embodiments, the linker can be an amino acid group that includes amino, thiol, and/or carboxylic groups. Some exemplary strategies for forming hydrolytically degradable linkers include:

(1) $\epsilon$-Amino group of lysine (which can be integrated into a polymer) and $\alpha$-amino group of a protein. The amine can be on the polymer backbone (with or without a spacer, e.g., PEG, or an alkyl chain). This can yield an amide, thiourea, alkylamine or urethane linkage.
(2) Thiol group or a free cysteine, which forms a thioether linkage.
(3) Thiol group on a cysteine, which can be conjugated with vinylsulfone (R—$SO_2$—CH=$CH_2$).
(4) Carboxylic acid groups on the aspartic and glutamic acid.

Some examples of hydrolytically degradable linkages include amide linkages that can be generated by reacting an amine group with succinate esters such as N-hydroxysuccinimide (NHS), thiol linkages such as disulfide (R-L1-S—S-L2-R') where the length of the linker L1 and L2 control the hydrolization, or ester bonds formed by coupling the peptide's carboxylic end with a hydroxyl on the polymer backbone (with or without a spacer, e.g., PEG, or an alkyl chain). Esterification can be carried out using established methods in the art (e.g., carbodiimide chemistry in the presence of 1-ethyl-3-(3-dimethylaminopropyl)carbodiimide (EDC)).

Enzymetically degradable linkers/linkages can be degraded by an enzyme, often to target a specific area of the body or organ. In other words, the stimulus for an enzymetically degradable linker is the presence of an enzyme. For example, a specific dipeptide sequence can be incorporated into the linker, which can be cleaved by an enzyme. Some examples of enzymetically degradable linkers or linkages include, but are not limited to, self-immolative p-aminobenzyloxycarbonyl (PABC) spacer between the dipeptide and the polymer, dipeptides such as phenylaniline-lysine and valine-cysteine, or PEG/dipeptide linkages such as alanyl-valine, alanyl-proline and glycyl-proline.

Some other linker/linkages can be found at "Biodegradable Polymers for Protein and Peptide Drug Delivery" Bioconjugate Chem. 1995, 6:332-351; M. P. Lutolf and J. A. Hubbell, Biomacromolecules 2003, 4:713-722; and U.S. patent application Ser. No. 10/871,658. Some additional representative linking chemistry is described in U.S. patent application Ser. No. 10/871,658, the entire disclosure of which is hereby incorporated by reference.

Coating Construct

In some embodiments, a coating can have a construct that allows it to have a controlled release of hydrophilic drug (e.g., a cRGD peptide) and a hydrophobic drug (e.g., an anti-proliferative agent (e.g., everolimus). The coating can include the hydrophilic drug and the hydrophobic drug in different layer of the coating.

In some embodiments, a base layer of coating can include a polymer with a polar block or segment and a hydrophilic drug and another layer of coating (e.g., a topcoat) can include a hydrophobic drug and a hydrophobic polymer. Examples of the polymer with a polar block or segment can be, but are not limited to, poly(urethane), poly(HEMA-block-MMA), poly(HEMA-block-HPMA), poly(HPMA-GFLG), poly(butyl methacrylate-co-ethylene glycol acrylate) (poly(BMA-block-PEGA)) or poly(MOEMA-block-HEMA). MOEMA is short for methoxyethyl methacrylate. HEMA is short for hydroxylethyl methacrylate. MMA is short for methyl methacrylate, HPMA is short for hydroxylpropyl methacrylate. HPMA-GFLG is HPMA terminated with the peptide sequence GFLG (glycine-pheylaniline-leucine-glycine) which is used as a linker. Examples of hydrophobic polymer include, but are not limited to, polymers or copolymers of vinyl monomers, and polymers or copolymers of fluorinated olefin (e.g., Solef™ polymers). In some embodiments, the hydrophobic polymer can also include a small percentage of units derived from a small percentage of a hydrophilic monomer. Some examples of such polymers include, but are not limited to, poly(MOEMA-HEMA) and poly(MOEMA-PEGA) with low percentage of HEMA or PEGA (e.g., <10 mol %). In these polymers, the hydrophobic portion of the polymer can control the release of everolimus while the small percentage units derived from a hydrophilic monomer can allow for slow release of cRGD.

The coating construct of these embodiments can be applied to any medical devices where the release of a hydrophobic drug and a hydrophilic drug must be achieved concurrently. In some embodiments, the hydrophilic drug is cRGD and the hydrophobic drug is an anti-proliferative agent such as everolimus. The release rate profile of the cRGD peptide with a burst will match the mechanistic temporal need for activation of EPC capture process. The long term release of the cRGD peptide at low doses can maintain the recruiting of EPCs and continue to affect the surrounding endothelial cells and smooth muscle cells. In addition, the burst of release can be controlled by decreasing or increasing the thickness of the topcoat, by using a sealant between the two layers, or by lowering the D:P in the cRGD peptide containing layer.

In some embodiments, the hydrophilic drug is a cRGD peptide and the hydrophobic drug is an anti-proliferative agent such as everolimus. The cRGD can be included in a topcoat of the coating while the anti-proliferative agent can be included in the base layer (aka reservoir layer). For example, the topcoat can be formed on top of an intermediate sealant-coat comprising a hydrophobic polymer (e.g., an acrylate or fluoropolymer). The reservoir layer can include everolimus. The coating construct of these embodiments can allow the everolimus and the cRGD to release from the coating at two different timescales. Note, the coating can also include a cRGD attached to a polymer in the reservoir layer such that the coating can provide a burst release of the cRGD peptide and a sustained release of the cRGD peptide. The release profile of cRGD peptide with a burst can match the mechanistic temporal need for activation of EPC capture process. The sustained release of the cRGD peptide can maintain the recruiting of EPCs and continue to affect the surrounding endothelial cells and smooth muscle cells.

In some embodiments, a coating can have a construct that has cRGD in the reservoir layer and an anti-proliferative agent (e.g., everolimus) in the topcoat. The construct may or may not have a sealant layer, depending on the targeted release of cRGD and/or everolimus from the coating.

Biocompatible Polymers

Any biocompatible polymer can form a coating with the hydrophilic drug and the hydrophobic drug described herein. The biocompatible polymer can be biodegradable (both bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and copolymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Biobeneficial Material

In some embodiments, the coating having the features described herein can include a biobeneficial material. The combination can be mixed, blended, or patterned or arranged in separate layers. The biobeneficial material useful in the coatings described herein can be polymeric or non-polymeric. The biobeneficial material is preferably non-toxic, non-antigenic and non-immunogenic enough so that it can be successfully introduced into a patient. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic-acid-bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG(PVDF-PEG), PLURONIC™ surfactants (polypropylene oxide-co-polyethylene glycol), poly (tetramethylene glycol), hydroxy functional poly(vinyl pyrrolidone), biomolecules such as fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

In some embodiments, in addition to the hydrophilic drug and the hydrophobic drug described above, the coating described herein can additionally include one or more bioactive agents. These bioactive agents can be any agent which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, or antioxidant properties.

These agents can be cystostatic agents, agents that promote the healing of the endothelium (other than by releasing or generating NO), or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. Capoten° and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE and ENDOTAK, available from Guidant Corporation, Santa Clara, Calif.), and devices facilitating anastomosis such as anastomotic connectors. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

In accordance with embodiments of the invention, the coating according to the present invention can be included in an implantable device or prosthesis, e.g., a stent. For a device including one or more active agents, the agent will retain on the device such as a stent during delivery and expansion of the device, and released at a desired rate and for a predetermined duration of time at the site of implantation.

Preferably, the device is a stent. The stent described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

Example 1

Coating constructs for Concurrent Release of cRGD and Everolimus

A coating construct according to the present invention can be formed according to the following configuration on a 18 mm Vision stent (available from Guidant Corporation, Santa Clara, Calif.):

Primer: 85 µg of PBMA;

Drug matrix: 595 µg of Biospan™, which is segmented polyurethane, and cRGD with a drug (cRGD)/polymer ratio (D:P) of 1:6;

Topcoat: 259 µg of Solef™ and everolimus (D:P=1:4.9).

In this example, the somewhat polar polyurethane backbone allows the polyurethane and the cRGD to dissolve in an organic solvent and then spray-coat onto a stent. The Solef™ layer controls the release of both cRGD and everolimus. The D:P ratios and the coating thicknesses can be adjusted to reach the appropriate release rates and doses for each of the two drugs. The polar polyurethane can be replaced with other polymers with polar blocks such as methacrylate block copolymers. Some examples of methacrylate block copolymers include, but are not limited to, poly(HEMA-block-MMA), poly(HEMA-block-HPMA), poly(HPMA-GFLG), poly(BMA-block-PEGA), or poly(MOEMA-block-HEMA).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device comprising a coating, the coating comprising
    a first layer comprising a hydrophilic drug and a polymer, the polymer having a polar block(s) or a polar segment(s); and
    a second layer comprising a hydrophobic drug and a hydrophobic polymer;
    wherein the coating includes the hydrophilic drug and the hydrophobic drug in different layers and provides a concurrent release profile of the hydrophilic drug and the hydrophobic drug;
    wherein the hydrophilic drug is a cRGD peptide;
    wherein the hydrophobic drug is sirolimus, everolimus, zotarolimus, or a combination thereof;
    wherein the polymer with a polar block(s) or segment(s) is selected from the group consisting of polyurethanes, poly(hydroxyethyl methacrylate-block-methyl methacrylate) (poly(HEMA-block-MMA)), poly(hydroxyethyl methacrylate-block-methyl methacrylate) (poly(HEMA-block-HPMA)), poly(hydroxypropyl methacrylate) terminated with glycine-pheylaniline-leucine-glycine (poly(HPMA-GFLG), poly(butyl methacrylate-block-poly(ethylene glycol) acrylate) (poly(BMA-block-PEGA)), poly(methoxyethyl methacrylate-block-hydroxyethyl methacrylate) (poly(MOEMA-block-HEMA)), and combinations of these; and
    wherein the hydrophobic polymer is a copolymer of MOEMA with PEGA or HEMA having a percentage of PEGA or HEMA below 10 mol %.

2. The medical device of claim 1, wherein the hydrophilic drug is attached to a polymer included in the coating.

3. The medical device of claim 2 wherein a linker attaches the hydrophilic drug to the polymer.

4. The medical device of claim 3 wherein the linker is a hydrolytically degradable linker or a proteolytically degradable linker.

5. The medical device of claim 3 wherein the linker is an enzymatically degradable linker.

6. The medical device of claim 3 wherein the linker comprises poly(ethylene glycol) (PEG) or an alkyl chain.

7. The medical device of claim 4, wherein the hydrolytically degradable linker is selected from the group consisting of an amide linkage, a thiol linkage, an ester linkage, a thiourea linkage, an alkylamine linkage, a urethane linkage, a thioether linkage and combinations thereof.

8. The medical device of claim 4, wherein the hydrolytically degradable linker comprises a cysteine unit, an aspartate unit, a glutamate unit, or a combination thereof.

9. The medical device of claim 3 wherein the linker is a biodegradable polymer.

10. The medical device of claim 5 wherein the enzymatically degradable linker comprises a dipeptide sequence.

11. The medical device of claim 10 wherein the enzymatically degradable linker comprises a spacer.

12. The medical device of claim 11 wherein the spacer is selected from the group consisting of p-aminobenzyloxycarbonyl (PABC), a dipeptide, PEG, and combinations thereof, and
    wherein the dipeptide is selected from the group consisting of phenylaniline-lysine, valine-cysteine, alanyl-valine, alanyl-proline, glycyl-proline and combinations thereof.

13. The medical device of claim 1 wherein the release profile of the hydrophilic drug of the first coating layer includes an initial burst release followed by sustained release.

14. The medical device of claim 1 wherein the release profile of the hydrophilic drug of the first coating layer is zero-order sustained release.

15. The medical device of claim 1, wherein the layer comprising the cRGD peptide is a base coat, and
    wherein the layer comprising everolimus, sirolimus, zotarolimus, or a combination thereof is a topcoat.

16. The medical device of claim 1,
    wherein the hydrophobic drug is everolimus,
    wherein the layer comprising the hydrophilic drug is a topcoat,
    wherein the layer comprising the hydrophobic drug is a base coat, and
    wherein the topcoat and the base coat are separated by a sealant layer comprising a hydrophobic polymer.

17. The medical device of claim 16, wherein the hydrophobic polymer of the sealant layer comprises a hydrophobic acrylate polymer or fluoropolymer.

18. The medical device of claim 1, further comprising another bioactive agent.

19. The medical device of claim 1 which is a stent.

20. The medical device of claim 2, which is a stent.

21. The medical device of claim 3, which is a stent.

22. The medical device of claim 1 which is a bioabsorbable stent.

23. The medical device of claim 2, which is a bioabsorbable stent.

24. The medical device of claim 3, which is a bioabsorbable stent.

25. A method of forming the medical device of claim 1, comprising forming a coating on the medical device comprising
    a first layer comprising a hydrophilic drug and a polymer, the polymer having a polar block(s) or a polar segment(s); and
    a second layer comprising a hydrophobic drug and a hydrophobic polymer;
    wherein the coating includes the hydrophilic drug and the hydrophobic drug in different layers and provides a concurrent release profile of the hydrophilic drug and the hydrophobic drug;
    wherein the hydrophilic drug is a cRGD peptide;

wherein the hydrophobic drug is sirolimus, everolimus, zotarolimus, or a combination thereof;

wherein the polymer with a polar block(s) or segment(s) is selected from the group consisting of polyurethanes, poly(hydroxyethyl methacrylate-block-methyl methacrylate) (poly(HEMA-block-MMA)), poly(hydroxyethyl methacrylate-block-methyl methacrylate) (poly(HEMA-block-HPMA)), poly(hydroxypropyl methacrylate) terminated with glycine-pheylaniline-leucine-glycine (poly(HPMA-GFLG), poly(butyl methacrylate-block-poly(ethylene glycol) acrylate) (poly(BMA-block-PEGA)), poly(methoxyethyl methacrylate-block-hydroxyethyl methacrylate) (poly(MOEMA-block-HEMA)), and combinations of these; and wherein the hydrophobic polymer is a copolymer of MOEMA with PEGA or HEMA having a percentage of PEGA or HEMA below 10 mol %.

26. A method of treating, or ameliorating a medical condition, comprising implanting in a human being the medical device of claim 1, wherein the medical condition is selected from the group consisting of atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, and combinations of these.

27. The medical device of claim 1, wherein the hydrophobic polymer is a copolymer of MOEMA with PEGA having a percentage of PEGA below 10 mol %.

28. The method of claim 25, wherein the hydrophobic polymer is a copolymer of MOEMA with PEGA having a percentage of PEGA below 10 mol %.

* * * * *